United States Patent [19]

Vrieland et al.

[11] Patent Number: 5,302,773
[45] Date of Patent: Apr. 12, 1994

[54] PROCESS OF OXIDIZING ALIPHATIC HYDROCARBONS EMPLOYING A MOLYBDATE CATALYST ENCAPSULATED IN A HARD, GLASSY SILICA MATRIX

[75] Inventors: G. Edwin Vrieland; Stephen J. Doktycz; Bijan Khazai, all of Midland, Mich.

[73] Assignee: The Dow Chemical Company, Midland, Mich.

[21] Appl. No.: 797,882

[22] Filed: Nov. 26, 1991

Related U.S. Application Data

[63] Continuation-in-part of Ser. No. 505,751, Apr. 6, 1990, Pat. No. 5,146,031, which is a continuation-in-part of Ser. No. 383,107, Jul. 20, 1989, Pat. No. 4,973,791.

[51] Int. Cl.$^5$ ............................ C07C 5/09; B01J 21/08
[52] U.S. Cl. ..................................... 585/624; 585/630; 585/631; 585/658; 585/663; 502/255; 502/254; 502/306
[58] Field of Search ............ 502/255, 254, 306; 585/624, 630, 631, 658, 663

[56] References Cited

U.S. PATENT DOCUMENTS

| | | |
|---|---|---|
| 2,423,681 | 7/1947 | Butterbaugh et al. |
| 2,426,118 | 8/1947 | Parker, Jr. et al. |
| 2,941,958 | 6/1960 | Connor, Jr. et al. |
| 3,119,111 | 1/1964 | McDonald et al. |
| 3,146,210 | 8/1964 | Baldwin |
| 3,180,903 | 4/1965 | Lindquist et al. |
| 3,488,402 | 1/1970 | Michaels et al. |
| 3,598,759 | 8/1971 | Bertolacini |
| 3,758,418 | 8/1973 | Leonard, Jr. et al. |
| 3,862,256 | 1/1975 | Isailingold et al. |
| 3,928,238 | 12/1975 | Koberstein et al. |
| 3,959,182 | 5/1976 | Izawa et al. |
| 4,035,417 | 7/1977 | Izawa et al. |
| 4,059,658 | 11/1977 | Shoup et al. |
| 4,112,032 | 9/1978 | Blaszyk et al. |
| 4,170,570 | 10/1979 | Zagata et al. |
| 4,229,604 | 10/1980 | Tmenov et al. |
| 4,276,196 | 6/1981 | Dalton et al. |
| 4,280,929 | 7/1981 | Shaw et al. |
| 4,388,223 | 6/1983 | Ferlazzo et al. |
| 4,447,558 | 5/1984 | Sasaki et al. |
| 4,453,006 | 6/1984 | Shaw et al. |
| 4,559,320 | 12/1985 | Reusser |
| 4,764,498 | 8/1988 | Wissner et al. |
| 4,895,821 | 1/1990 | Kainer et al. |
| 4,902,442 | 2/1990 | Garces |
| 4,914,073 | 4/1990 | Grimm et al. |
| 4,966,877 | 10/1990 | Langerbeins et al. |
| 4,973,791 | 11/1990 | Vrieland et al. ............... 585/624 |

FOREIGN PATENT DOCUMENTS

0225062  6/1987  European Pat. Off.

OTHER PUBLICATIONS

Chemical Abstracts 88-136328/20 (1986).
Chemical Abstracts 104:131946b (1986).
Chemical Abstracts 86-316078/48 (1985).
Chemical Abstracts 85-232465/38 (1984).
Chemical Abstracts 86-096610/15 (1984).
Derwent 91463R-AE (1970).

*Primary Examiner*—Patrick P. Garvin
*Assistant Examiner*—E. D. Irzinski
*Attorney, Agent, or Firm*—Marie F. Zuckerman

[57] ABSTRACT

A process for preparing olefins and diolefins in high productivity which involves contacting an aliphatic hydrocarbon, such as butane, with a heterogeneous catalyst composition containing reactive oxygen under reaction conditions sufficient to produce a more highly unsaturated aliphatic hydrocarbon, such as 1,3-butadiene. The catalyst composition contains a glassy silica matrix of specified surface area and macro-porosity into which are encapsulated domains of a catalyst component containing oxides of magnesium and molybdenum. The catalyst has high crush strength and is useful in transport reactors.

38 Claims, No Drawings

PROCESS OF OXIDIZING ALIPHATIC HYDROCARBONS EMPLOYING A MOLYBDATE CATALYST ENCAPSULATED IN A HARD, GLASSY SILICA MATRIX

CROSS REFERENCE TO RELATED APPLICATIONS

This application is a continuation-in-part of application Ser. No. 505,751, filed Apr. 6, 1990, and now U.S. Pat. No. 5,146,031 which is a continuation-in-part of application Ser. No. 383,107, filed Jul. 20, 1989, now U.S. Pat. No. 4,973,791, issued Nov. 27, 1990.

BACKGROUND OF THE INVENTION

This invention pertains to the oxidation of aliphatic hydrocarbons, such as alkanes and monoolefins, in the presence of a molybdate catalyst to form more highly unsaturated aliphatic hydrocarbons.

Unsaturated aliphatic hydrocarbons, such as monoolefins and diolefins, are useful as monomers and comonomers in the preparation of polyolefin plastics.

U.S. Pat. No. 3,119,111 discloses a process for the oxidative dehydrogenation of a $C_4$ to $C_6$ alkane having a four carbon chain to a 1,3-alkadiene. The reaction occurs in the presence of oxygen and a catalyst containing an alkali metal molybdate, such as lithium molybdate. It is taught that the catalyst can be employed with a carrier material, such as powdered alumina. Disadvantageously, this process requires potentially explosive mixtures of alkanes and oxygen. More disadvantageously, the catalyst of this process contains a high concentration of alkali metal which lowers catalytic activity.

U.S. Pat. No. 3,180,903 discloses a process for the dehydrogenation of aliphatic hydrocarbons containing from two to five carbon atoms. Butanes, for example, can be converted to butenes and butadienes. The catalyst is taught to contain chromium oxides or molybdenum oxides supported on a gel-type alumina. Optionally, the catalyst may contain one or more alkali metal oxides. Disadvantageously this process is limited to a low hydrocarbon conversion and a low ultimate yield of butadiene.

U.S. Pat. No. 3,488,402 teaches the dehydrogenation of butane to butene and butadiene in the presence of two catalysts. The first is a dehydrogenation catalyst containing alumina, magnesia, or combinations thereof, promoted with an oxide of a metal of Groups IVB, VB or VIB, such as chromia, vanadium oxide or molybdenum oxide. The second catalyst is an oxidation catalyst comprising a Group TVA or VA vanadate, molybdate, phosphomolybdate, tungstate or phosphotungstate. Disadvantageously, this process comprises two steps and requires subatmospheric pressures. Even more disadvantageously, this process produces low butadiene selectivity and yield.

U.S. Pat. No. 3,862,256 discloses a process for the oxidative dehydrogenation of paraffin hydrocarbons, such as butane, over a catalyst containing oxy compounds of molybdenum and magnesium and up to 20 weight percent silicon oxide. When butane is contacted with the catalyst, the products include butenes and butadiene; however, the selectivity and space-time yield of butadiene are lower than desired. In addition, the feed contains hydrocarbon and oxygen, which is not desirable for safety reasons. Finally, the magnesium oxide support does not possess the strength and attrition resistance needed for fluid bed or transport reactors.

U.S. Pat. No. 4,229,604 discloses a process for the oxidative dehydrogenation of a paraffin, such as butane, to unsaturated hydrocarbons, such as butenes and butadiene. The catalyst contains molybdenum and magnesium oxides which may be impregnated into a carrier consisting of granulated porous crystalline silica modified with alkali carbonate. The catalyst may comprise up to 20 percent by weight carrier. It is taught that during carrier preparation silicates of the alkali metals are formed. It is further taught that on the surface of the catalyst there exists an active magnesium molybdate. Disadvantageously, the catalyst produces a selectivity and space-time yield of butadiene which are too low for industrial use.

U.S. Pat. No. 4,388,223 discloses the oxidizing dehydrogenation of butene-1 to butadiene. The catalyst comprises (a) a crystalline phase (I) consisting of one or more molybdates belonging to the monoclinic system, chosen from ferric, aluminum, cerium, and chromium molybdates, (b) a crystalline phase (II) consisting of one or more molybdates belonging to the monoclinic system, including magnesium molybdate, and (c) one or more promoter elements including vanadium. It is also taught that the catalyst may comprise alkaline elements such as potassium, lithium, cesium and magnesium and/or acidic elements, such as phosphorus and silicon. In one embodiment the catalytic metallic salts are used to impregnate microspheroidal silica. In another embodiment a soluble colloidal silicate is added to the solution of catalytic metallic salts, and the mixture is spray dried and thermally activated to obtain the catalyst. This process co-feeds hydrocarbon and oxygen, which is undesirable for safety reasons. Moreover, the catalyst does not have the strength and attrition resistance required for fluid-bed or transport reactors.

While the oxidation of aliphatic hydrocarbons is well researched in the prior art, the selectivity and space-time yield to particular unsaturated hydrocarbons, such as diolefins, fall short of those which are desired for commercial exploitation. Moreover, the catalysts employed in the prior art do not possess the strength and attrition resistance required for use in industrial fluid bed or transport reactors. Accordingly, it would be desirable to have a selective, direct oxidation of an aliphatic hydrocarbon, such as an alkane or monoolefin, to the corresponding unsaturated aliphatic hydrocarbons, specifically the diolefin. It would be more desirable if such an oxidation produced a high selectivity and high productivity of the diolefin and other olefins, and correspondingly low selectivities to deep oxidation products, such as carbon dioxide. Finally, it would be most desirable if the above-identified process could be accomplished with a catalyst having a high strength and attrition resistance so as to be useful in a commercial scale fluid bed or transport reactor.

SUMMARY OF THE INVENTION

In one aspect, this invention is a process of preparing an unsaturated aliphatic hydrocarbon comprising contacting an aliphatic hydrocarbon having at least three carbon atoms with a catalyst of this invention, described hereinafter. Under the reaction conditions of the process of this invention more unsaturated aliphatic hydrocarbons, such as diolefins, are formed in a productivity of at least about 0.15 gram per gram catalyst per hour (g/g cat-hr).

Advantageously, aliphatic hydrocarbons can be oxidized directly to more highly unsaturated aliphatic hydrocarbons by the process of this invention. Surprisingly, the process of this invention produces a high selectivity and high productivity of more highly unsaturated aliphatic hydrocarbons, especially diolefins, and low selectivities and low yields of undesirable deep oxidation products, such as carbon monoxide and carbon dioxide. In a preferred aspect, butadiene can be produced directly from butane in high selectivity and high productivity by the process of this invention while maintaining low selectivities of deep oxidation products. For the purposes of this invention, the "productivity" is defined as the grams of unsaturated aliphatic hydrocarbon(s) produced per gram catalyst per hour.

Unsaturated aliphatic hydrocarbons, such as monoolefins and diolefins, are useful as monomers or comonomers in the formation of polyolefins. Butadiene is also potentially useful as an intermediate in the preparation of styrene.

In a second aspect, this invention is a solid heterogeneous catalyst composition containing reactive oxygen. The composition comprises a glassy silica matrix having a Brunauer-Emmett-Teller (BET) surface area no greater than about 20 $m^2/g$ and having macropores in the range from about 500 Å to about 4000 Å in diameter, as determined by methods described in detail hereinafter. The silica matrix comprises from about 25 to about 90 weight percent of the catalyst composition. Encapsulated into the silica matrix are domains of a catalyst component comprising magnesium oxide and molybdenum oxide. The above-identified catalyst composition exhibits a crush strength of at least about 0.60 lb.

The catalyst composition of this invention is useful in the above-identified process of oxidizing aliphatic hydrocarbons to more unsaturated aliphatic hydrocarbons. Advantageously, the catalyst composition of this invention achieves a high productivity to unsaturated aliphatic hydrocarbons when compared with catalysts of the prior art. More advantageously, the catalyst of this invention is strong and hard. Consequently, the catalyst composition disclosed herein possesses the activity and strength required for use in commercial fluid bed and transport reactors, such as riser reactors.

In a third aspect, this invention is a process of preparing the above-identified catalyst composition comprising (a) treating a source of magnesium oxide with a blocking agent, (b) adding the treated source of magnesium oxide to an alkali metal silicate solution, the silicate being present in a concentration sufficient to provide silica in an amount ranging from about 25 to about 90 weight percent of the catalyst composition, (c) polymerizing the silicate to form a composite material comprising a glassy silica matrix having a BET surface area no greater than about 20 $m^2/g$ and having macropores ranging from about 500 Å to about 4000 Å in diameter, the matrix containing domains of the treated source of magnesium oxide, (d) ion-exchanging the composite material with an ammonium salt to reduce the concentration of alkali metal ions, (e) drying and calcining the composite material under conditions sufficient to remove the blocking agent and sufficient to convert the source of magnesium oxide into magnesium oxide, (f) impregnating the domains of magnesium oxide with a source of an oxide of molybdenum and optionally a promoting amount of a source of an oxide of alkali metal, (g) calcining the resulting impregnated composite material under conditions sufficient to convert the sources of an oxide of molybdenum and oxide of alkali metal to an oxide of molybdenum and an oxide of alkali metal.

In a fourth aspect, this invention is a process of preparing a hard composite material comprising a glassy silica matrix having a BET surface area no greater than about 20 $m^2/g$ and having macropores ranging from about 500 Å to about 4000 Å in diameter, the silica matrix having encapsulated therein domains of a metal oxide phase. The process comprises (a) treating a source of the metal oxide with a blocking agent, the metal oxide being selected from those which are reactive with an alkali metal silicate, (b) adding the treated source of the metal oxide to an alkali metal silicate solution, (c) polymerizing the silicate to form a composite material comprising a glassy silica matrix having a BET surface area no greater than about 20 $m^2/g$ and having macropores ranging from about 500 Å to about 4000 Å in diameter, the matrix containing domains of the treated source of metal oxide phase, and (d) calcining the composite material under conditions sufficient to remove the blocking agent and sufficient to convert the source of metal oxide into metal oxide. In this manner the above-identified hard composite material is produced having a crush strength of at least about 0.60 lb.

The above-identified process of preparing a hard composite material is useful for preparing a metal oxide encapsulated in silica without forming a significant quantity of unwanted metal silicate. Thus, the process is especially useful when the metal oxide and silica are reactive and, without the blocking agent, would form significant quantities of metal silicate. The composite materials are useful as strong and hard catalysts or catalyst supports.

DETAILED DESCRIPTION OF THE INVENTION

The aliphatic hydrocarbons which can be employed in the process of this invention include alkanes and olefins which have three or more carbon atoms.

The alkanes can be alternatively described as paraffin hydrocarbons. These compounds are known to those skilled in the art as saturated hydrocarbons. As noted hereinbefore, the alkanes contain at least three carbon atoms, and additionally, can have straight-chain or branched structures. Typically, the alkane contains up to about 20 carbon atoms. Examples of suitable alkanes include n-butane, n-pentane, n-hexane, n-heptane, n-octane, n-nonane, n-decane, n-dodecane, and higher saturated homologues, as well as isobutane, isopentane, neopentane, and likewise branched hexanes, heptanes, octanes, nonanes, decanes, dodecanes, and higher branched homologues. Certain alicyclic hydrocarbons are suitable reactants, and therefore, for the purposes of this invention are included herein. Some examples of alicyclic hydrocarbons include cyclobutane, cyclopentane, cyclohexane, cycloheptane, cyclooctane, methylcyclopentane, methylcyclohexane and other alkyl-substituted cycloalkanes. Preferably, the alkane is normal or linear.

The olefins can be further described as aliphatic hydrocarbons containing at least one unsaturated double bond. As noted earlier, the olefins should also contain at least three carbon atoms, and typically up to about 20 carbon atoms. The location of the double bond is not critical; therefore, the double bond can occur at a terminal or internal location along the carbon chain. Preferably, however, the olefin has a normal or linear structure, rather than a branched structure. For example, 1-butene is preferred over isobutylene. Thus, some examples of suitable olefins include, 1-butene, 2-butene, 1-pentene, 2-pentene, 3-pentene, 1-hexene, 2-hexene, 3-hexene, and likewise 1-heptene, 1-octene, 1-nonene, 1-decene, and isomers thereof wherein the unsaturation occurs at any other position along the carbon chain. Olefins containing more than one double bond, such as 1,3-hexadiene and isoprene, are also acceptable, being converted in the process of this invention to more highly unsaturated hydrocarbons. Certain alicyclic olefins, such as cyclohexene and vinylcyclohexene, are also suitable starting materials, and therefore, for the purposes of this invention are included herein. Preferably, the olefin is a monoolefin. More preferably, the olefin is 1- or 2-butene. Alkynes are not suitable reactants for the process of this invention.

The many specific examples of aliphatic hydrocarbons, noted hereinabove, are representative of those which are suitable for the process of this invention, and are not intended to be limiting thereof. Other aliphatic hydrocarbons may be available to one skilled in the art and may also be suitable for the process of the invention.

The preferred alkanes are normal paraffins which can be represented by the general formula:

$$CH_3-(CH_2)_n-CH_3$$

wherein n is an integer from 1 to 8. More preferably, n is an integer from 2 to 6. Most preferably, n is 2, and the alkane is n-butane.

Optionally, the aliphatic hydrocarbon reactant can be diluted with a non-reactive gas, such as nitrogen, helium, argon, methane, carbon dioxide or steam. While the type of diluent is determined by prevailing economic considerations, a preferable diluent is nitrogen. If a diluent is used, the amount can vary widely depending upon the design of the reactor and the capacity of the solid oxidant. The hydrocarbon content of the hydrocarbon-diluent mixture typically ranges from 1 mole percent to 100 mole percent. Preferably, the hydrocarbon content of the mixture ranges from about 10 mole percent to about 100 mole percent, more preferably, from about 40 mole percent to about 100 mole percent.

The catalyst composition of this invention, described in detail hereinbelow, is a solid heterogeneous oxide at least d portion of the oxygen of which is reactive. By this it is meant that a labile form of oxygen is present in the catalyst, and that this labile form of oxygen is capable of oxidizing the aliphatic hydrocarbon. Thus, in one aspect the catalyst of this invention is a solid oxidant. After the labile oxygen is removed through reaction, the catalyst is spent. Moreover, the catalyst may build up over time a carbonaceous residue on its surface. The spent and poisoned catalyst can be regenerated by contact with a source of gaseous oxygen. Thus, in addition to the aliphatic hydrocarbon, oxygen is required for the catalytic process of this invention.

Oxygen is typically supplied from a gaseous source provided as a continuous oxygen-containing feed. Any source of oxygen i3 acceptable, such as pure gaseous elemental oxygen, air, or nitrous oxide. The preferred source of oxygen is gaseous air. Optionally, the gaseous elemental oxygen can be diluted with a non-reactive gas, such as nitrogen, helium, argon, or carbon dioxide. Preferably, the diluent is nitrogen. If a non-reactive diluent is employed, the oxygen content of the mixture is preferably not greater than about 50 mole percent. More preferably, the oxygen content of the mixture ranges from about 0.5 mole percent to about 30 mole percent. Most preferably, the oxygen content of the mixture ranges from about 1 mole percent to about 20 mole percent.

The amount of oxygen employed in the catalytic process of this invention is any amount which is (1) sufficient to oxidize fully the solid heterogeneous catalyst, and (2) sufficient to remove carbonaceous residues from the catalyst's surface. Preferably, the regeneration of the catalyst is carried out separately from the oxidation of the aliphatic hydrocarbon.

Alternatively, it is acceptable to co-feed a small amount of gaseous elemental oxygen with the aliphatic hydrocarbon. The function of the co-feed is to burn off carbonaceous residues on the surface of the catalyst, to replenish to some extent the reactive oxygen of the catalyst, and to burn off any hydrogen which is formed in the process. The concentration of oxygen in the aliphatic hydrocarbon and oxygen feed is limited by the explosive limits of this mixture. Preferably, the oxygen concentration is maintained outside the lower explosive limit.

The solid heterogeneous catalyst composition of this invention comprises a hard silica matrix and a catalytic component. The silica matrix can be characterized as a glassy silica having a BET surface area no greater than about 20 m$^2$/g. The term "glassy" means that the silica is an amorphous and disordered phase, as determined by X-ray diffraction (XRD). Additionally, the silica can be characterized as a dense phase, meaning that it does not contain a measurable density of micropores or mesopores. A typical micropore ranges in size from about 4 Å to about 20 Å, while a typical mesopore ranges from about 20 Å to about 200 Å. The silica of this invention does, however, contain a random system of macropores characterized by large pores on the order of about 500 Å to about 4000 Å in diameter. In a visual sense, the topology of the silica is best compared to that of a sponge or irregular honeycomb. The catalytic component comprises an oxide of molybdenum and an oxide of magnesium, at least partially combined as magnesium molybdate. Preferably, the catalytic component consists essentially of an oxide of molybdenum and an oxide of magnesium. The catalytic component occurs as discrete domains of magnesium oxide containing molybdenum oxide, the domains being encapsulated in the silica matrix. The domains of the catalyst component range in size from about 0.1 μm to about 500 μm. Optionally, the catalytic component may also contain a promoting amount of alkali metal and/or an oxide of vanadium.

The silica in the above-identified heterogeneous catalyst acts as an inert and hard matrix, thereby imparting a high crush strength and attrition resistance to the catalyst so that it is suitable for use in fluid bed or transport reactors. The magnesium oxide functions in a dual role: first, as a support for the active catalyst component comprising magnesium oxide and molybdenum oxide, and secondly, a3 a base. It is believed that basicity enhances the desorption of olefinic products in the oxydehydrogenation process. The molybdenum oxide contributes significantly to the catalyst's activity, especially as combined with magnesium oxide in the form of magnesium molybdate. The alkali metal promoter functions to increase the basicity of the catalyst thereby increasing the selectivity to higher unsaturates in the process of this invention. The alkali metal promoter is a Group IA metal compound. Small amounts of other elements may be present in the catalyst, provided that these elements do not materially change the performance of the catalyst.

As a first step in preparing the catalyst composition of this invention, magnesium oxide is encapsulated into the aforementioned silica matrix. This preparation presents certain challenges. U.S. Pat. No. 3,678,144 teaches a method of preparing a glassy silica body having certain metal oxides bound into the silica network. The patent is silent with respect to magnesium oxide. It has now been discovered that when magnesium oxide powder is blended into an aqueous potassium silicate solution with a gellation agent according to the method of U.S. Pat. No. 3,678,144, the aqueous silicate is readily absorbed onto the surface of the magnesium oxide forming silica and magnesium silicates. The resulting hard composite material exhibits significantly reduced activity in the oxydehydrogenation process of this invention. It is believed that the reduced activity is related to the presence of the surface silicates. Surprisingly, it has now been further discovered that if good phase separation exists between the magnesium oxide and silica, it is possible to maintain an active magnesium oxide surface.

In view of the above and in another aspect, this invention is a method of preparing a composite material comprising a glassy silica matrix having encapsulated therein domains of magnesium oxide. The aforementioned method is easily generalized for preparing a glassy silica matrix having encapsulated therein discrete domains of a reactive metal oxide phase. The term "reactive" means that the metal oxide or a source of the metal oxide is capable of reacting with the alkali metal silicate from which the silica is derived or reacting with silica itself to form metal silicates. The method of this invention comprises (a) treating a source of a metal oxide with a blocking agent, the metal oxide being selected from those which are reactive with an alkali metal silicate, (b) adding the treated source of metal oxide to an alkali metal silicate solution, (c) polymerizing the silicate to form a composite material comprising a glassy silica matrix having a BET surface area no greater than about 20 m$^2$/g and having macropores ranging in size from about 500 Å to about 4000 Å, the silica matrix having encapsulated therein domains of the source of metal oxide treated with blocking agent, and (d) calcining the composite material under conditions sufficient to remove the blocking agent and sufficient to convert the source of metal oxide into metal oxide. Optionally, the composite material may be ion-exchanged with an ammonium salt after the polymerization step (Step c) and prior to the calcination step (Step d) to reduce the concentration of alkali metal ions. Advantageously, in this preparative process the formation of deactivating surface silicates is significantly reduced. Moreover, good phase separation exists between the metal oxide and silica when compared with the process of U.S. Pat. No. 3,678,144 which does not employ blocking agent.

Any source of metal oxide is suitable for the preparation of the composite material provided that the metal oxide itself is reactive with an alkali metal silicate. The metals of Groups IIA, IIIA, IVA, and VA provide suitable reactive oxides, the group designations (IIA, IIIA, etc.) following the recommendations of the former IUPAC. Preferably, the metals are selected from the group consisting of magnesium, titanium, zirconium and niobium. More preferably, the metal is magnesium. Aside from the oxides themselves, suitable sources of such oxides include the hydroxides, halides, nitrates, sulfates, acetates, and carbonates of the selected metal. Preferred sources include the metal oxides and hydroxides. Even more preferably, the source of metal oxide is an oxide or hydroxide of magnesium, titanium, niobium or zirconium. Most preferably, the source of metal oxide is magnesium hydroxide or magnesium oxide. It is also beneficial for the particle size of the magnesium hydroxide to range from about 0.1 μm to about 500 μm, preferably, from about 1 μm to about 250 μm.

The blocking agent may be any organic compound with a plurality of functional groups containing oxygen or nitrogen. Non-limiting examples include polyols, poly(carboxylic acids), polyanhydrides, polyamines, polyamides, polyesters, polyethers, and other polyhydroxylated compounds, such as cellulosies and starches. Polymers based on phenolic or phenolformaldehyde resins may also be used. Preferred blocking agents include poly(vinyl alcohol) and polyacrylic and polymethacrylic acids or salts. More preferred is poly(vinyl alcohol) having a molecular weight ranging from about 1000 to about 500,000. Most preferred is poly(vinyl alcohol) having a molecular weight ranging from about 14,000 to about 115,000, available as 75-100 percent hydrolyzed acetate groups.

Typically, the blocking agent is dissolved in a suitable solvent to form a solution, and the source of metal oxide is mixed into the solution to form a second solution or gel or paste. Any solvent is acceptable provided that it is inert with respect to the blocking agent and source of metal oxide. Water is the preferred solvent, but acetone, alcohols, and other common organic solvents are also acceptable. The concentration of the blocking agent in the solvent usually ranges from about 1 weight percent to about 50 weight percent. The source of metal oxide is generally added slowly and with a high degree of agitation to the solution containing the blocking agent. The amount of blocking agent employed typically ranges from about 1 to about 20 weight percent of the weight of the source of metal oxide. The resulting solution or gel or paste is dried at a temperature in the range from about 50° C. to about 200° C. for a time sufficient to remove the solvent and form a dried solid. Thereafter, the solid is crushed and sieved to a fine powder. At this stage, a transmission electron micrograph (TEM) of the powder typically reveals that some of the particles of the source of metal oxide are coated with a layer of blocking agent, the thickness commonly ranging from about 0.1 μm to about 1 μm. Other particles, however, do not show any coating, and it is believed that the coating is thinner than the detectable limit, possibly on the order of one monolayer in thickness.

After the source of metal oxide is treated with blocking agent, the treated source is blended into an aqueous alkali metal silicate solution and the silicate is polymerized. Suitable alkali metal silicate solutions and polymerization conditions are specified in U.S. Pat. No. 3,678,144, and therefore the relevant sections of that patent are incorporated herein by reference. For example, the suitable alkali silicates include lithium silicate, sodium silicate, and potassium silicate. In order to maintain the silica in solution, the concentration of the alkali metal must be sufficient to yield a solution having a pH greater than about 10. Preferably, the alkali silicate solution is a potassium silicate solution, more preferably, a commercially available potassium silicate solution containing 8.3 weight percent $K_2O$ and 20.0 weight percent $SiO_2$, the balance being water. Optionally, colloidal silica may be used in combination with the alkali silicate solution. The amount of colloidal silica which may be blended with the alkali silicate ranges form about 0 to about 30 weight percent of the total silica present.

The metal oxide source, treated with blocking agent, is blended into the alkali silicate solution very slowly and with a high degree of agitation to ensure that the solution remains smooth and fluid. The amount of alkali silicate solution, and optional colloidal silica, employed is sufficient to provide silica in the range from about 25 to about 90 weight percent based on the weight of the calcined composite material, preferably from about 35 to about 70 weight percent. The actual value will vary depending upon the end use of the Composite material. In the preferred application involving a catalyst containing magnesium and molybdenum oxides for butane oxidation, the silica concentration ranges from about 25 to about 90 weight percent based on the weight of the calcined catalyst composition.

A gellation agent is required for the polymerization of the silicate. The gellation agent functions to reduce the pH of the silicate solution by neutralizing the alkali metal ions which are present, and thereafter the silica polymerizes. Suitable gellation agents include formamide, formaldehyde, paraformaldehyde, glyoxal, ethyl acetate, and methyl acetate. Preferably, the gellation agent is formamide. Since the rate of polymerization varies with the specific gellation agent, it may be added to the alkali silicate solution either before or after the addition of the treated metal oxide source. If the gellation agent is added first, then the polymerization should not reach completion before the metal oxide source is fully blended. For example, if the gellation agent is formamide, it is usually added to the silicate solution prior to the addition of metal oxide. If the gellation agent is ethyl acetate, it should be added after the addition of metal oxide. The concentration of gellation agent is related to the concentration of alkali ions present. Typically, the concentration ranges from about 1 to about 10 weight percent based on the weight of the alkali silicate solution, preferably from about 2 to about 5 weight percent.

There are different ways of handling the viscous mixture containing the alkali silicate, the treated metal oxide source and the gellation agent. In one method, the mixture is heated in a batch in a drying oven typically under a nitrogen purge at a temperature ranging from about 70° C. to about 120° C. Normally the mixture sets to a hard mass within at least about 1 hour, at which time it may be broken into smaller pieces and cured. The curing process generally includes heating at a temperature in the range from about 100° C. to about 225° C. for a time ranging from about 2 hr to about 10 hr. Post cure, the dried composite is usually crushed and sieved to a powder having a particle size in the range from about 177 $\mu$m to 1190 $\mu$m (80 to 14 mesh). The particles of dried powder comprising the treated source of metal oxide encapsulated in the above-identified matrix of silica, are typically irregular in shape.

Alternatively, the viscous mixture containing the treated source of metal oxide, the gellation agent, and the alkali silicate may be suspension polymerized to yield spheroidal beads or balls having a size in the range from about 200 $\mu$m to about 1500 $\mu$m. Spheroidal particles are preferred for fluid-bed transport reactors. In this method, the mixture is added to an immiscible liquid, typically a chlorinated hydrocarbon, such as The Dow Chemical Company's DOWTHERM E® o-dichlorobenzene, at a temperature in the range from about 5° C. to about 100° C., preferably from about 10° C. to about 80° C. The addition may be effected by simply pouring the mixture into the immiscible liquid with sufficient agitation to disperse the mixture into droplets or by injecting the mixture through a droplet-forming nozzle. In order to prevent coalescence of the spheres, fumed silica may be added as a suspension agent to the chlorinated hydrocarbon. Bead size is controlled by the stirring rate of the shear mixer. Typically, a shear rate of about 300 rpm to about 725 rpm is used. This method yields hard, spheroidal beads comprising regions of the treated source of metal oxide isolated within the above-described silica matrix.

As a third alternative, the viscous mixture containing the treated source of metal oxide, the gellation agent, and the alkali silicate can be spray-dried to form spheroidal particles ranging in diameter from about 10 $\mu$m to about 250 $\mu$m. For industrial scale applications the spray-drying method is preferred. Any spray-drying equipment which is conventionally used to produce catalyst particles for fluidized bed reactors may be employed. For example, a Niro Atomizer S-12.5R/N spray drying apparatus, with a means for controlling the inlet and outlet temperatures, is acceptable.

Analysis of the composite material following polymerization of the silicate reveals good phase separation between the source of metal oxide and the silica matrix. For example, a backscattered electron image of a material produced by the polymerization of silicate in the presence of poly(vinyl alcohol)-blocked magnesium hydroxide reveals a silica/magnesium hydroxide composite. The corresponding elemental Mg map shows areas of high magnesium concentration which are identified as discrete magnesium hydroxide particles. The corresponding elemental Si map reveals that essentially no silicon resides in areas of high magnesium concentration. Additionally, potassium levels are much higher in the silicon rich areas than in areas of high magnesium concentration, as illustrated by elemental K mapping. From these data it is concluded that good separation of the magnesium hydroxide and silica phases is Present. Transmission electron micrographs of the above-identified magnesium hydroxide/silica composite show predominantly crystalline magnesium hydroxide bounded by a dense, glassy silica. Again, good phase separation exists for at least about 80 percent of the composite. Up to 20 percent of the silica may appear as crystalline fines, which may contain some magnesium; however, not enough magnesium is present to indicate formation of magnesium silicate.

If desired, the composite can be leached or treated with solvents to remove the metal oxide from the silica matrix to yield a pure silica matrix. This procedure simply requires that the composite be soaked in an acid solution. In the absence of the domains of metal oxide, the silica gives the appearance of a sponge or irregular honeycomb. The BET surface area of the silica is no greater than about 20 $m^2/g$, preferably no greater than about 10 $m^2/g$, more preferably no greater than about 5 $m^2/g$. At the lower limit it is possible for the surface area to be as low as 0.2 $m^2/g$. The BET method for determining surface area is described by R. B. Anderson in *Experimental Methods in Catalytic Research*, pp. 48-66, Academic Press, 1968. As noted hereinbefore, the silica matrix essentially does not contain a microporous or mesoporous structure; however, a large macroporous structure randomly permeates the matrix. The macropores range in diameter from 500 Å to about 4000 Å, as determined by mercury infusion techniques using, for example, a Micromeritics Model 9305 mercury porosimeter.

The composite comprising the silica matrix and the treated metal oxide may contain alkali metal ions derived from the alkali silicate solution. Accordingly, the composite will have basic properties. Should a less basic, neutral or acidic composite be desired, the composite may be ion-exchanged with an acid solution or an ammonium salt, such as ammonium nitrate, to the desired degree of acidity. In the case of the catalyst composition of this invention, the concentration of alkali metal ions may be reduced via ion-exchange to levels less than about 0.5 weight percent, preferably, less than about 0.1 weight percent. The ion-exchange procedure is conducted after polymerization of the silicate (Step c) and prior to calcination (Step d). The molarity of the acid or ammonium salt solution is typically low, preferably ranging from about 0.1 M to about 2 M. The pH of the solution is typically in the range from about 7.5 to about 9.0, preferably in the range from about 8.2 to about 8.9. The ion-exchange procedure may be carried out simply by stirring the composite in a flask filled with the ion-exchange solution or by passing the solution through a column filled with composite. At least two ion-exchanges are preferred, and more may be beneficial.

Following the optional removal of alkali ions, the composite is dried for about 2 hr to about 10 hr at a temperature between about 60° C. and about 150° C. Thereafter, the composite is calcined at a temperature ranging from about 400° C. to about 800° C. for a period of about 1 hr to about 10 hr to remove the blocking agent and to convert the source of metal oxide to the metal oxide. After calcination a composite material is obtained comprising the above-described silica matrix having encapsulated therein discrete regions of metal oxide phase. Calcination does not significantly change the morphology or surface area of the silica matrix. For the specific case of magnesium oxide, the BET surface area of the magnesium oxide phase ranges from about 70 m$^2$/g to about 170 m$^2$/g. Accordingly, the calcined composite material has a BET surface area ranging from about 30 m$^2$/g to about 150 m$^2$/g.

The calcined composite comprising the silica matrix and metal oxide can be impregnated with any catalytic metal or metal compound to form a hard catalyst composition. For example, a composite comprising the silica matrix and magnesium oxide can be impregnated with a solution containing a source of molybdenum oxide to form a strong catalyst composition which is active in the hydrocarbon oxydehydrogenation process Of this invention. The impregnation technique is described by Charles N. Satterfield in *Heterogeneous Catalys is in Practice*, McGraw-Hill Book Company, New York, 1980, pp. 82-83, which is incorporated herein by reference. Any source of molybdenum oxide is acceptable, including for example, MoO$_3$, (NH$_4$)$_2$Mo$_2$O$_7$, (NH$_4$)$_6$Mo$_7$O$_{24}$·4H$_2$O, and (NH$_4$)$_2$MoO$_4$. The molybdenum oxide can also be obtained from a precursor molybdenum compound, such as molybdenum carbonyls, e.g., MoO(CO)$_6$. Preferably, the molybdenum is in the +6 oxidation state. Preferably, the source of molybdenum oxide is ammonium heptamolybdate represented by the formula (NH$_4$)$_6$Mo$_7$O$_{24}$·4H$_2$O. Generally, the desired quantity of a molybdenum oxide or precursor compound is dissolved in a solvent, preferably water, to make a solution. The solution is brought into contact with the composite material and the resulting slurry is dried to remove solvent. If the solution is aqueous, the drying is conducted in an oven at a temperature in the range from about 70° C. to about 120° C. Thereafter, the dried slurry is calcined to form a catalytically active composition containing the silica matrix, magnesium oxide and molybdenum oxide. The calcination is typically conducted at a temperature ranging from about 300° C. to about 900° C. for a time ranging from 0.5 hour to about 24 hours. Preferably, the calcination is conducted at a temperature in the range from about 500° C. to about 800° C., more preferably, from about 550° C. to about 650° C. Alternatively, the dried slurry, described hereinabove, can be employed directly with no prior calcination in the catalytic process of this invention. Since the molybdenum precursor can be converted into molybdenum oxide at or about 300° C., and since the catalyst bed is heated to a temperature higher than about 300° C., the dried composition will be converted in situ into the catalytically active magnesium and molybdenum oxides. As noted hereinbefore, calcination essentially does not change the basic morphology of the composite. The molybdenum oxide is associated with the magnesium oxide particles and not with the silica matrix, as shown by TEM.

The elemental analysis of the calcined solid reveals a composition ranging from about 3 weight percent MoO$_3$ to about 30 weight percent MoO$_3$, from about 72 weight percent MgO to about 7 weight percent MgO, and from about 25 weight percent silica to about 90 weight percent silica. Preferably, the composition ranges from about 5 weight percent MoO$_3$ to about 25 weight percent MoO$_3$, from about 25 weight percent MgO to about 70 weight percent MgO, and from about 25 weight percent silica to about 70 weight percent silica. More preferably, the composition ranges from about 10 weight percent MoO$_3$ to about 20 weight percent MoO$_3$, from about 30 weight percent MgO to about 55 weight percent MgO, and from about 35 weight percent silica to about 50 weight percent silica.

It is beneficial to add a promoting amount of at least one alkali metal promoter to the catalyst component. The promoter serves to increase the selectivity and productivity of unsaturated products, e.g. diolefins, in the process of this invention. Such a promoter is typically a compound of lithium, sodium, potassium, rubidium, cesium or francium of sufficient basicity to improve the selectivity to higher unsaturates in the process of this invention. Suitable compounds include the alkali oxides, hydroxides and carbonates. Compounds which decompose on heating to the oxides are also suitable, such as alkali metal acetates and oxalates. Alkali metal salts may be found which are also suitable, although typically, the alkali metal halides and alkali metal silicates are not preferred due to their lower basicity. Preferably, the alkali metal promoter is an alkali metal oxide, hydroxide, carbonate, acetate, or oxalate. More preferably, the alkali metal promoter is an oxide or hydroxide of potassium or cesium. Most preferably, the alkali metal promoter is an oxide or hydroxide of potassium.

The amount of alkali metal promoter significantly affects the selectivity of the catalyst. Generally, any amount of alkali metal promoter is acceptable which is sufficient to increase the selectivity and the productivity of unsaturated products, such as diolefins, in the process of this invention. Typically, the amount of alkali metal promoter calculated as the alkali hydroxide is in the range from about 0.01 weight percent to about 5 weight percent based on the combined weights of silica, magnesium oxide and molybdenum oxide. Preferably, the amount of alkali metal promoter calculated as the alkali metal hydroxide is in the range from about 0.02 weight percent to about 2 weight percent, more preferably, in the range from about 0.1 weight percent to about 1.0 weight percent, based on the combined weights of silica, magnesium oxide and molybdenum oxide. Below the lower preferred amount of alkali metal promoter the selectivity to diolefin is reduced while the selectivity to deep oxidation products is increased. Above the upper preferred amount of alkali metal promoter the selectivity and productivity to diolefin are also reduced.

The alkali metal promoter can be added to the catalyst component in a variety of ways known to those in the art. For example, the promoter can be applied by the impregnation technique, noted hereinbefore. In this technique the molybdenum-impregnated composite is immersed in a solution of the alkali metal promoter, for example, a methanolic solution of the alkali metal oxide or hydroxide. The alkali-impregnated composite is then drained of excess solution, dried in an oven to remove residual solvent, and calcined at a temperature in the range from about 550° C. to about 650° C. Alternatively, the alkali metal compound can be impregnated from the same solution as the molybdenum compound.

Optionally, the catalyst component of this invention can contain an activator which functions to increase the activity of the catalyst at any given temperature. Preferably, the activator does not decrease significantly the selectivity to diolefins and monoolefins. Preferably, the activator allows the reaction to be run at a lower temperature, while achieving high selectivity and high productivity of diolefins. Activators which are suitable for incorporation into the catalyst include the oxides of vanadium, preferably $V_2O_5$. Any amount of vanadium oxide can be added to the catalyst provided that (1) the activity of the catalyst is increased, and (2) the selectivity for alkenes, including mono- and diolefins, is not significantly decreased. Generally, if an activator is used, the concentration ranges from about 0.05 weight percent to about 10 weight percent based on the total weight of the catalyst composition. Preferably, the concentration of activator ranges from about 0.10 weight percent to about 5.0 weight percent, more preferably, from about 0.15 weight percent to about 2.0 weight percent. The activator can also be applied to the composite by the impregnation technique.

The process of this invention can be carried out in any suitable reactor, including batch reactors, continuous fixed-bed reactors, surry reactors, fluidized bed reactors, and riser reactors. Preferably, the reactor is a continuous flow reactor, such as a continuous fixed-bed reactor or a transport reactor of the type described hereinafter.

The preferred commercial reactor for the process of this invention is a transport bed reactor, such as a riser reactor. In such reactors the catalyst particles are subjected to constant impact with other catalyst particles and with the walls of the reactor. Such forces gradually reduce the size of the catalyst particles to small fines which are lost in the reaction products; thus, the useful lifetime of the catalyst is greatly limited. Consequently, it is required for the catalyst to be prepared in a form which is able to withstand high impact and erosion forces. The catalyst composition of this invention possesses the strength and attrition resistance required for commercial use.

Typically, the riser reactor comprises an upright vessel of relatively low ratio of diameter to length. The catalyst is continuously charged into the bottom of the riser reactor. Likewise, the aliphatic hydrocarbon feedstream is delivered concurrently to the bottom of the riser reactor as a vapor phase feed or as a liquid phase feed. Preferably, the alkane is delivered as a vapor phase feed premixed with an inert, gaseous diluent, and optionally, a small concentration of oxygen. The feed moves upward through the reactor, thereby contacting the catalyst. Upon contacting the catalyst, the feed is converted into a mixture of products, including monoolefins, diolefins, higher unsaturated olefins, cracking products, deep oxidation products, such as carbon monoxide and carbon dioxide, and heavies, such as benzene and furan in the case of a butane feed. The product stream exits the riser reactor and is separated by known methods, such as distillation, to recover the desired products, typically the diolefins. Unreacted alkanes and monoolefin products are recycled to the riser reactor for further oxidation.

Riser reactor technology is advantageous for the process of this invention, because (1) the hazard of using a feedstream containing a mixture of alkane and/or olefin and elemental oxygen is eliminated, and (2) the selectivity for diolefins is enhanced, especially at the high temperatures required for this process. In contrast, if a feedstream of alkane and oxygen is employed at a high temperature and a high oxygen/alkane mole ratio, there is a tendency to produce more deep oxidation products, such as carbon monoxide and carbon dioxide. In addition, the danger of a run-away reaction is greater.

The operation of a riser reactor can be simulated by employing a method of alternating pulses. Thus, a pulse of the hydrocarbon-containing feed is passed through the catalyst bed where it is oxidized to form the desired olefin products. Next, a pulse of inert gas is passed through the catalyst bed to purge the bed of residual alkanes and alkenes. After purging, a pulse of oxygen-containing feed is passed through the catalyst bed to regenerate the catalyst. Finally, a second pulse of inert gas is passed through the catalyst bed to purge the bed of oxygen, after which the cycle is repeated. Such a procedure is employed in the illustrative embodiments, described hereinafter.

The aliphatic hydrocarbon reactant is contacted with the catalyst at any operable temperature which promotes the oxidation process of this invention and yields the desired unsaturated products. Typically, the temperature is in the range from about 400° C. to about 700° C. Preferably, the temperature is in the range from about 500° C. to about 650° C. More preferably, the temperature is in the range from about 530° C. to about 600° C. Below the preferred lower temperature the conversion of reactant may be low. Above the preferred upper temperature the selectivity and productivity of diolefin products may decrease.

Likewise, the aliphatic hydrocarbon reactant is contacted with the catalyst at any operable pressure which promotes the oxidation process of this invention and yields the desired unsaturated products. Typically, the partial pressure of the reactant is adjusted to maintain the reactant in the vapor state at the operating temperature. Preferably, the partial pressure of the aliphatic hydrocarbon is in the range from about subatmospheric to about 100 psig. More preferably, the partial pressure is in the range from about 1 psig to about 30 psig. Most preferably, the partial pressure is in the range from about 3 psig to about 15 psig.

When the process of this invention is conducted in a continuous flow reactor, described hereinbefore, the flow rate of the reactants can be varied. Generally, in the process of this invention the aliphatic hydrocarbon reactant is fed into the reactor at any operable flow rate which promotes the oxidation reaction and yields the desired conversion and selectivity of unsaturated products. The flow rate is expressed as the gas hourly space velocity (GHSV) and is given in units of volume of aliphatic hydrocarbon-containing gaseous feed per total reactor volume per hour or simply $hr^{-1}$. Typical values vary from about 100 $hr^{-1}$ to about 20,000 $hr^{-1}$. Preferably, the GHSV ranges from about 100 $hr^{-1}$ to about 500 $hr^{-1}$. It should be understood that the space velocity controls the residence time of the reactants. In a riser reactor, for example, a gas residence time less than about 10 seconds is preferred, while times less than about 5 seconds are more preferred and less than about 1 second are most preferred.

For the case of the riser reactor, the spent catalyst leaves the top of the reactor and is transported into a second reactor for regeneration. Regeneration is effected by contact with oxygen. Typically, a preheated oxygen source, like that described hereinbefore, is fed into the bottom of the second reactor. The spent catalyst is contacted with the oxygen source at any operable temperature, pressure, and oxygen-source flow rate which are sufficient to regenerate the catalyst. The process variables should be controlled, however, so as to prevent a runaway reaction or the buildup of excessive heat. Preferably, the temperature is in the range from about 500° C. to about 700° C., more preferably, in the range from about 550° C. to about 650° C. Preferably, the pressure is in the range from subatmospheric to about 100 psig, more preferably, in the range from about 2 psig to about 50 psig. The oxygen-source flow rate will depend upon the heat transfer properties of the particular reactor. For example, at some high flow rates the temperature may rise dramatically resulting in an uncontrolled reaction.

When the aliphatic hydrocarbon is contacted with the catalyst of this invention, an oxidation of the aliphatic hydrocarbon occurs resulting in the loss of at least two hydrogen atoms from the hydrocarbon reactant with formation of by-product water. The organic products which are produced are predominantly unsaturated aliphatic hydrocarbons, such as monoolefins and diolefins. These unsaturated products usually contain the same number of carbon atoms as the reactant aliphatic hydrocarbon. Thus, these products are not products of cracking, which would contain fewer carbon atoms than the starting hydrocarbon. Generally, also, the unsaturated products possess a higher degree of unsaturation than the reactant hydrocarbon. For example, alkane3, such as butane, can lose two hydrogen atoms to yield monoolefins, such as 1-butene, trans-2-butene, and cis-2-butene. In turn, monoolefins, such as the butenes previously cited, can lose two hydrogen atoms to form 1,3-butadiene.

The preferred diolefin products can be represented by the general formula:

$$CH_2=CH-CH=CH-(CH_2)_m-H$$

wherein m is an integer from 0 to about 6. Preferably, m is an integer from 0 to about 2. More preferably, m is 0 and the unsaturated product is 1,3-butadiene. Isomers of the formula shown hereinabove can also be formed wherein the unsaturation occurs at any other location along the carbon chain. Preferably, the unsaturation occurs in a conjugated fashion, as exemplified in the product 1,3-butadiene. Even more unsaturated variants of the general formula can be formed wherein further oxidation has occurred to yield more than two ethylenic double bonds. Alkynes, however, are not formed in significant amounts.

In addition to alkenes, the product stream can contain by-products of various types. For example, when the saturated alkane is n-butane, small quantities of cracking products, such as propylene and ethylene, can be formed, as well as heavies, such as benzene and furan, and deep oxidation products, such as carbon monoxide and carbon dioxide. Unexpectedly, however, these by-products, especially the deep oxidation products, are significantly reduced over the prior art processes.

For the purposes of this invention, "Conversion" is defined as the mole percentage of aliphatic hydrocarbon reactant lost from the feed stream as a result of reaction. The conversion can vary widely depending upon the reactants, the form of the catalyst, and the process conditions such as temperature, pressure, flow rate, and catalyst residence time. Within the preferred temperature range, as the temperature increases the conversion generally increases. Within the preferred gas hourly space velocity range, as the space velocity increases the conversion generally decreases. Typically, the conversion of the aliphatic hydrocarbon is at least about 10 mole percent. Preferably, the conversion is at least about 20 mole percent; more preferably, at least about 30 mole percent; even more preferably, at least about 40 mole percent; and most preferably, at least about 50 mole percent.

Likewise, for the purposes of this invention "selectivity" is defined as the mole percentage of converted carbon which forms a particular product. Selectivities also vary widely depending upon the reactants, the form of the catalyst, and the process conditions. Typically, the process of this invention achieves high selectivities to diolefins. Within the preferred temperature range, as the temperature increases the selectivity for alkenes generally decreases. Within the preferred space velocity range, as the space velocity increases the selectivity for alkenes generally increases. Preferably, the combined selectivity to all alkenes is at least about 50 mole percent; more preferably, at least about 60 mole percent; even more preferably, at least about 70 mole percent; most preferably, at least about 80 mole percent. Typically, the selectivity to diolefins is at least about 40 mole percent. Preferably, the selectivity to diolefins is at least about 50 mole percent, more preferably, at least about 60 mole percent, most preferably, at least about 70 mole percent.

The concept of simultaneous high conversion and high selectivity can be conveniently expressed in terms of yield. For the purposes of this invention, the term "yield" refers to the numerical product of the single-pass conversion and selectivity. For example, a process according to the present invention operating at a conversion of 0.65, or 65 mole percent, and a selectivity to diolefin of 0.75, or 75 mole percent, would have a diolefin yield of 0.49, or 49 mole percent. Typically, the yield of diolefin achieved in the process of this invention is at least about 8 mole percent. Preferably, the yield of diolefin achieved in the process of this invention is at least about 18 mole percent, more preferably at least about 28 mole percent, most preferably, at least about 35 mole percent. Typically, in the oxidation of butane the yield of total $C_4$ olefins is at least about 20 mole percent. Preferably, in the oxidation of butane the yield of total $C_4$ olefins is at least about 30 mole percent, more preferably, at least about 35 mole percent, most preferably, at least about 40 mole percent.

The rate at which a desired product is produced in the process of this invention can be expressed in the concept of space-time yield. For the purposes of this invention the "space-time yield" is defined as the mole percentage yield of a given product per hour (yield $hr^{-1}$), and it is the numerical product of the single-pass conversion, the selectivity, the gas hourly space velocity, and the concentration of the aliphatic hydrocarbon in the feedstream, wherein the conversion, selectivity and concentration are expressed as decimal fractions. Preferably, the space-time yield of diolefin in the process of this invention for a 20 volume percent alkane feed is at least about 30 percent per hour, more preferably, at least about 60 percent per hour, and most preferably, at least about 80 percent per hour.

Another measure of the rate at which a desired product is produced is the "productivity," defined as the grams unsaturated aliphatic hydrocarbon(s) formed per gram catalyst per hour (g/g cat-hr). Preferably, the productivity of butadiene in this process is at least about 0.10 g/g cat-hr, more preferably, at least about 0.25 g/g cat-hr. Preferably, the combined productivities of all of the unsaturated aliphatic hydrocarbons, such as C4 olefins, is at least about 0.15 g/g cat-hr, more preferably, at least about 0.20 g/g cat-hr, most preferably, at least about 0.30 g/g cat-hr.

Illustrative Embodiments

Testing the attrition resistance of a catalyst requires having on hand a large amount of catalyst sample. It is desirable to have a simple test procedure for small catalyst samples which gives an indication of attrition resistance. A test of crush strength is such a procedure, because increased crush strength suggests better attrition resistance.

Crush strength can be tested on any conventional equipment designed for such a purpose, however, a materials testing frame capable of providing a constant crosshead movement rate and a load capacity of at least 50 lb is preferred. For example, a suitable testing frame is an Instron 1125 instrument with a 20,000 lb capacity. This frame can be equipped with a 200 lb compression load cell with a stainless steel compression platen. A 1 cm diameter compression jig is designed and built to screw in directly to the bottom portion of the machine crosshead. A strip chart or computer data acquigition system is suitable for monitoring the load versus crosshead displacement.

Prior to testing, the load cell is balanced and calibrated. This is completed with the cell/platen in the compression testing configuration. The load cell is allowed to equilibrate for at least 15 minutes prior to calibration. Preferred instrument settings are the following: crosshead speed, 0.02 inches/min; chart speed, 2.0 inches/min; load cell range setting, 0–10 lb full scale. The specimen is centered on the load cell platen just below the compression jig. The crosshead is carefully lowered by manual control until minimal clearance between the fixture and specimen is achieved. Each specimen is tested at room temperature until the first sign of failure is observed (drop in load). The maximum load observed by the specimen is determined by the strip chart or computer data system.

The composite material or catalyst composition to be tested is sized into particles ranging from about 500 $\mu$m to about 800 $\mu$m. These particles are calcined at 600° C. for 2 hours prior to testing. Care should be taken to select particles of similar size for testing, and regular shaped particles are preferred. Typically, a minimum of ten specimens is tested for each sample. The crush strength of the catalyst of this invention is typically at least about 0.60 lb, preferably, at least about 0.80 lb, more preferably, at least about 1.00 lb, and most preferably, at least about 1.25 lb, as measured on a particle having a size in the range from about 500 $\mu$m to about 800 $\mu$m.

The following examples are illustrative of the process and catalyst of this invention, but are not intended to be limiting thereof. All percentages are given in mole percent carbon, unless noted otherwise.

EXAMPLE 1 —COMPOSITE MATERIAL AND CATALYST PREPARATION

A. Preparation of the Composite Material

A 5 weight percent poly(vinyl alcohol) (PVA) solution is prepared by adding PVA (26 g; MW 115,000; 100 percent hydrolyzed ester) to cold water (500 g) with rapid stirring and heating to 90° C. Magnesium hydroxide powder (90 g) is added to the PVA solution (200 g) with rapid mechanical stirring to form a creamy suspension. The suspension is dried in a nitrogen-purged oven at 80° C. for 18 hr, and the resulting PVA-treated magnesium hydroxide solid is rough crushed and heated further at 125° C. for 4 hr. The dried solid is fine crushed to pass a 170 mesh screen (88 $\mu$m).

With rapid mechanical stirring, formamide (3 g) is added slowly to a potassium silicate solution (100 g; 20.8 weight percent $SiO_2$, 8.3 weight percent K20) to form a clear solution free of gel clusters. The PVA-treated magnesium hydroxide powder (50 g), prepared hereinabove, is added gradually to the silicate solution to form a well-mixed slurry. The slurry is poured into a plastic beaker, covered with a watch glass to slow evaporation, and placed in an oven at 80° C. for about 45 minutes. During this time, the silicate polymerizes in the batch taking the form of the beaker. The polymerized material is removed and cut into chunks which are cured and dried for 18 hr at 80° C. The hardened chunks are crushed to a size ranging from about 177 $\mu$m to about 1190 $\mu$m (80–14 mesh). The crushed particles (70 ml) are loaded into a column and washed four times with 150 ml portions of an aqueous ammonium nitrate solution (1 M; pH 8). The wet particles are then slurried twice in 1 M ammonium nitrate, filtered, slurried twice with acetone, and filtered again. This procedure is designed to remove water located in the pores which could fracture the particles during heating. The filtered particles are air dried at room temperature and dried further at 80° C. for 6 hr. Elemental analysis of the particles indicates that the potassium level is less than 0.1 weight percent. The particles are further dried and calcined as follows: 2 hr at 100°–150° C., 4 hr at 150°–300° C., 1 hr at 300°–400° C., 4 hr at 400°–450° C., 2 hr at 450°–600° C., and 4 hr at 600°–610° C. A composite material is obtained comprising a silica matrix having domains therein of magnesium oxide, as determined by TEM. The silica matrix is characterized as having a BET surface area of 1 m²/g and a random macropore system wherein the diameter of the pores is in the range from about 3000 Å to about 4000 Å. The domains of magnesium X-1 oxide exhibit a BET surface area of 140 m²/g.

B. Preparation of the Catalyst

An aqueous solution containing 25 weight percent ammonium heptamolybdate (AHM) (23 g, 20 weight percent as $MoO_3$) adjusted to pH 8.5 is added to the composite material prepared hereinabove (30 g). The wetted material is dried overnight in flowing nitrogen at 80° C. and then calcined in air as follows: 2 hr at 100°–150° C., 4 hr at 150°–600° C., and 4 hr at 600–6100C to yield a catalyst composition comprising the above-identified silica matrix having domains therein of magnesium oxide containing molybdenum oxide. The catalyst contains 40.00 weight percent $SiO_2$, 16.67 weight percent $MoO_3$, the remainder being MgO. The crush strength of the catalyst, as measured on an Instron #IV crush strength instrument, gives a maximum load of 1.38 ±0.44 lb for spheroidal particles of 600 Jim size. By comparison, commercial alumina beads of approximately the same size, which are suitable for use in a transport reactor, exhibit a maximum load of 1.53±0.64 lbs. Thus, the strength of the catalyst composition of this invention is sufficient for use in a transport reactor.

EXAMPLE 2 — BUTANE OXIDATION

A catalyst similar to the one prepared in Example 1(B) is employed in the oxidation of butane in the following manner: approximately 15 cc of catalyst are loaded into a Vycoro reactor tube (18 mm OD ×7.6 cm length). The temperature of the reaction is measured from a stainless steel thermowell (⅛ inch OD) embedded in the catalyst sample. A feedstream containing butane (10–20 volume percent) and helium (90–80 volume percent) is passed over the catalyst for about 5–10 seconds. The flow of the feedstream is stopped and a purge stream comprising pure helium is passed over the catalyst at the same flow rate for 1 minute. The purge stream is stopped and a stream of oxygen (20 volume percent) in helium i3 passed over the catalyst at the same flow rate for 1 minute, followed by another purge stream of helium for 1 minute. This cycle is repeated and the combined products are collected in a Saran ® polyvinylidene chloride plastic bag for analysis. Analysis is performed on a Carle gas chromatograph designed to analyze for $C_1$–$C_5$ alkanes, alkenes and alkadienes, as well as permanent gases such as $N_2$, $O_2$, CO, $CO_2$, $H_2$, and heavier products including furan, benzene, and $C_6$ compounds. Isobutane is mixed with the feed or products as a standard. "Unknowns" are obtained from the difference between the carbon balance and 100 percent. The process conditions and results are set forth in Table I.

TABLE I [1]

| Example | 2 | 3 | 4 |
|---|---|---|---|
| Wt. Catalyst, g | 9.79 | 10.26 | 8.96 |
| Wt. % $SiO_2$ | 40.00 | 34.00 | 40.00 |
| GHSV, hr$^{-1}$ | 1060 | 994 | 994 |
| Pulse, sec | 5.0 | 10 | 10 |

TABLE I [1] -continued

| Example | 2 | 3 | 4 |
|---|---|---|---|
| % Conversion | 54.75 | 40.07 | 22.52 |
| % Selectivities: | | | |
| 1-butene | 3.46 | 4.77 | 8.64 |
| tr-2-butene | 3.11 | 3.95 | 9.09 |
| cis-2-butene | 2.53 | 4.28 | 7.87 |
| butadiene | 71.72 | 71.53 | 65.85 |
| Sum $C_4$'s | 80.82 | 84.53 | 91.45 |
| propylene | 0.00 | 0.27 | 1.23 |
| ethylene | 0.00 | 1.78 | 2.14 |
| % Total Cracking | 0.00 | 2.05 | 3.36 |
| $CO_2$ | 11.88 | 9.00 | 4.43 |
| CO | 4.42 | 3.64 | 0.77 |
| % Deep Oxidation | 16.30 | 12.64 | 5.19 |
| furan/benzene | 0.93 | 0.78 | 0.00 |
| Unknown | 1.97 | 0.00 | 0.00 |
| % Total Heavies | 2.89 | 0.78 | 0.00 |
| Total C balance | 98.92 | 100.09 | 101.7 |
| g $C_4$/g cat-hr | 0.30 | 0.23 | 0.16 |
| g $C_4$/g cat-hr [2] | 0.26 | 0.20 | 0.12 |
| % Yield $C_4$'s | 44.25 | 33.87 | 20.60 |

[1] Butane, 20 vol. %; Rxn. temperature, 580° C.
[2] BD is butadiene.

It is seen that the catalyst composition containing the above-described silica matrix and oxides of magnesium and molybdenum i3 highly active and selective in the oxidation of butane to butenes and butadiene (BD).

EXAMPLE 3 — CATALYST PREPARATION AND BUTANE OXIDATION

A catalyst composition is prepared as in Example 1, with the exception that magnesium oxide (90 g) is used instead of magnesium hydroxide during PVA treatment and PVA-treated magnesium oxide powder (34 g) is added to the potassium silicate solution. The composition thus prepared is essentially identical to the composition of Example 1. Moreover, the catalyst composition prepared with magnesium oxide exhibits a crush strength comparable to the crush strength of the catalyst composition in Example 1 and is therefore suitable for use in a riser reactor. The catalyst prepared with magnesium oxide is tested in the oxidation of butane according to the procedure of Example 2 with the results set forth in Table I. It is seen that the catalyst is highly selective and active in the oxidation of butane to butenes and butadiene.

EXAMPLE 4 — CATALYST PREPARATION AND BUTANE OXIDATION

Magnesium oxide (60 g) is added with mixing to a solution containing water (120 g) and 21 weight percent polyacrylic acid (50 g; 90,000 MW). The mixture is dried in a nitrogen-purged oven at 80° C. for 18 hr. The resulting polyacrylic acid-treated magnesium oxide is rough crushed, heated further at 125° C. for 4 hr, and crushed again to pass a 170 mesh screen (88 μm). The solid obtained is blended into a potassium silicate solution which is polymerized as in Example 1. The resulting composite is washed with ammonium nitrate, impregnated with a solution of ammonium heptamolybdate and calcined, per Example 1, to yield a catalyst composition of adequate hardness for use in a riser reactor. The catalyst composition is essentially identical to that of Example 1 and contains the above-identified silica matrix and domains of a catalyst component comprising magnesium oxide and molybdenum oxide.

The above-identified catalyst is tested in the oxidation of butane according to the procedure of Example 2 with the results set forth in Table I. It is seen that the catalyst composition prepared with a blocking agent of polyacrylic acid instead of poly(vinyl alcohol) is also highly active and selective in the oxidation of butane to butenes and butadiene (BD).

EXAMPLE 5 —CATALYST PREPARATION AND BUTANE OXIDATION

A catalyst composition is prepared as in Example 1 with the exception that the slurry containing poly(vinyl alcohol)-treated magnesium hydroxide, formamide and potassium silicate is suspension polymerized into spheroidal particles rather than polymerized in batch. The suspension polymerization method involves adding the slurry slowly at 10°-12° C. to o-dichlorobenzene (The Dow Chemical Company Dowtherm E ®), which additionally contains 1 percent by weight fumed silica as a dispersion agent. The mixture is then agitated using a low shear mixer for a period of time sufficient to break the aqueous phase into droplets. The temperature is then raised to 80° C. for 1.5 hr during which time the silicate cures to form spheroidal particles. The particles are washed with acetone to remove the Dowtherm E ®. Thereafter, the particles are aged for 18 hr, washed, dried and calcined as per Example 1. Specifically, the calcination is conducted for 2 hr at 100°-150° C., 4 hr at 150°-300° C., 1 hr at 300°-400° C., 4 hr at 400°-450° C., 2 hr at 450°-600° C., and 4 hr at 600°-610° C. The resulting catalyst composition comprises a silica matrix essentially identical to that described in Example 1. Encapsulated in the matrix are domains of magnesium oxide containing molybdenum oxide. The crush strength of the spheroidal particle is 1.34 lb ±0.29 lb, as measured on a particle of about 600 μm. It is seen that the composition prepared by suspension polymerization is strong enough for use in a riser reactor.

The catalyst prepared hereinabove is tested in the oxidation of butane according to the procedure of Example 2 with the results set forth in Table II. It is seen that the catalyst composition is highly active and selective in the oxidation of butane to butenes and butadiene (BD).

TABLE II [1]

| Example | 5 | 6 | 7 |
|---|---|---|---|
| Wt. Catalyst, g | 11.40 | 11.00 | 11.00 |
| Wt. % SiO$_2$ | 35.0 | 35.0 | 35.0 |
| Wt. % K$^+$, g | 0.0 | 0.1 | 0.2 |
| GHSV, hr$^{-1}$ | 994 | 1039 | 1026 |
| % Conversion | 49.03 | 43.19 | 35.67 |
| % Selectivities: | | | |
| 1-butene | 3.46 | 4.68 | 7.02 |
| tr-2-butene | 2.77 | 3.65 | 4.86 |
| cis-2-butene | 2.31 | 3.76 | 4.75 |
| butadiene | 57.07 | 64.49 | 66.69 |
| Sum C$_4$'s | 65.63 | 76.59 | 83.33 |
| propylene | 1.41 | 0.00 | 1.01 |
| ethylene | 1.96 | 2.37 | 2.78 |
| % Total Cracking | 3.38 | 3.43 | 3.79 |
| CO$_2$ | 18.00 | 11.14 | 5.85 |
| CO | 8.85 | 5.54 | 2.79 |
| % Deep Oxidation | 26.85 | 16.69 | 8.65 |
| furan/benzene | 4.13 | 2.52 | 1.97 |
| Unknown | 0.00 | 0.76 | 2.25 |
| % Total Heavies | 4.13 | 3.28 | 4.22 |
| Total C balance | 100.53 | 99.67 | 99.19 |
| g C$_4$/g cat-hr | 0.20 | 0.21 | 0.19 |
| g BD/g cat-hr [2] | 0.17 | 0.17 | 0.15 |
| % Yield C$_4$'s | 32.18 | 33.08 | 29.72 |

[1] Butane, 20 vol. %; Rxn. T, 580° C.; 10 sec pulse.
[2] BD is butadiene.

EXAMPLE 6 —CATALYST PREPARATION AND BUTANE OXIDATION

A catalyst composition (11.0 g) prepared as in Example 5 is impregnated with a solution comprising methanol (5.84 g) and potassium hydroxide (0.018 g). The impregnated catalyst is dried and calcined as in Example 5 to yield a catalyst composition having a potassium concentration of 0.1 weight percent. The crush strength of the catalyst gives a maximum load of 1.34 lb ±0.29 for spheroidal particles of 600 μm size. It is seen that the strength of the potassium-doped catalyst is sufficient for use in a transport reactor.

The catalyst is tested in the oxidation of butane according to the method of Example 2 with the results set forth in Table II. It is seen that the potassium-promoted catalyst composition achieves high selectivity and productivity for butenes and butadiene. When Example 6 is compared with Example 5 it is seen that the catalyst composition containing potassium achieves a significantly higher selectivity to C$_4$ olefins with only a slight reduction in conversion.

EXAMPLE 7 —CATALYST PREPARATION AND BUTANE OXIDATION

A catalyst composition prepared and impregnated with potassium as in Example 6 is impregnated again with a solution comprising methanol (5.84 g) and potassium hydroxide (0.018 g). The impregnated composition is dried overnight and calcined as in Example 5 to yield a composition containing 0.2 weight percent potassium. The crush strength of the spheroidal catalyst particles of 600 μm size is 1.34±0.29, therefore the composition is suitable for use in a riser reactor. The catalyst composition is employed in the oxidation of butane with the results shown in Table II. It is seen that the potassium-promoted catalyst composition achieves high selectivity and productivity for butenes and butadiene.

What is claimed is:

1. A process of preparing an unsaturated aliphatic hydrocarbon comprising contacting an aliphatic hydrocarbon having at least three carbon atoms with a solid heterogeneous catalyst composition having reactive oxygen and having a crush strength of at least about 0.60 lb, the catalyst composition comprising a glassy silica matrix having a BET surface area no greater than about 20 m$^2$/g and having macropores ranging in size from about 500 Å to about 4000 Å, the silica matrix comprising from about 25 to about 90 weight percent of the catalyst composition and having encapsulated therein domains of a catalyst component comprising an oxide of magnesium and an oxide of molybdenum, the contacting occurring under conditions such that an unsaturated aliphatic hydrocarbon is produced in a productivity of at least about 0.15 g/g cat-hr.

2. The process of claim 1 wherein the aliphatic hydrocarbon is an alkane represented by the general formula:

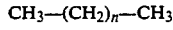

$$CH_3-(CH_2)_n-CH_3$$

wherein n is an integer from 1 to about 8.

3. The process of claim 2 wherein n is 2 and the alkane is n-butane.

4. The process of claim 1 wherein the aliphatic hydrocarbon is diluted with a non-reactive gas.

5. The process of claim 4 wherein the hydrocarbon concentration ranges from about 40 mole percent to about 100 mole percent.

6. The process of claim 1 wherein the catalytic component consists essentially of an oxide of magnesium and an oxide of molybdenum.

7. The process of claim 1 wherein the oxide of magnesium and the oxide of molybdenum are partially combined in the form of magnesium molybdate.

8. The process of claim 1 wherein the temperature is in the range from about 400° C. to about 700° C.

9. The process of claim 1 wherein the aliphatic hydrocarbon partial pressure is in the range from about subatmospheric to about 100 psig.

10. The process of claim 1 wherein the gas hourly space velocity of the feedstream is in the range from about 100 hr$^{-1}$ to about 20,000 hr$^{-1}$.

11. The process of claim 1 wherein the unsaturated aliphatic hydrocarbon is a diolefin and wherein the diolefin is represented by the general formula:

$$CH_2=CH-CH=CH-(CH_2)_m-H$$

wherein m is an integer from 0 to about 6.

12. The process of claim 11 wherein m is 0 and the diolefin is 1,3-butadiene.

13. The process of claim 1 wherein the catalyst composition has a productivity of at least about 0.2 g unsaturated aliphatic hydrocarbons/g cat-hr.

14. The process of claim 1 wherein the catalyst component contains a promoting amount of an alkali metal promoter.

15. The process of claim 14 wherein the alkali metal promoter is an alkali metal oxide, hydroxide, carbonate, acetate, or oxalate.

16. The process of claim 14 wherein the alkali metal is cesium.

17. The process of claim 14 wherein the alkali metal is potassium.

18. The process of claim 14 wherein the concentration of the alkali metal promoter is in the range from about 0.01 weight percent to about 5 weight percent calculated as the alkali hydroxide and based on the combined weights of silica, magnesium oxide and molybdenum oxide.

19. The process of claim 18 wherein the concentration of alkali metal promoter is in the range from about 0.02 weight percent to about 2 weight percent.

20. A process of preparing 1,3-butadiene comprising contacting n-butane with a solid heterogeneous catalyst composition containing reactive oxygen and having a crush strength of at least about 0.60 lb, said catalyst comprising a glassy silica matrix having a BET surface area no greater than about 20 m$^2$/g and having macropores ranging in diameter from about 500 Å to about 4000 Å, the silica matrix comprising from about 25 to about 90 weight percent of the catalyst composition and having encapsulated therein domains of a catalytic component comprising magnesia and molybdenum oxide, the contacting occurring at a temperature in the range from about 500° C. to about 650° C., and a pressure in the range from about 1 psig to about 30 psig and under such other reaction conditions that a mixture of products is formed containing 1,3-butadiene in a productivity of at least about 0.10 g/g cat-hr.

21. The process of claim 20 wherein the selectivity to butadiene is at least about 60 mole percent.

22. The process of claim 20 wherein the selectivity to butadiene is at least about 70 mole percent.

23. The process of claim 20 wherein the productivity of butadiene is at least about 0.2 g/g cat-hr.

24. The process of claim 20 wherein the concentration of silica in the catalyst composition ranges from about 35 to about 50 weight percent.

25. The process of claim 20 wherein the crush strength of the catalyst composition is at least about 1.00 lb.

26. A solid heterogeneous catalyst composition capable of providing a reactive form of oxygen and having a crush strength of at least about 0.60 lb, the composition comprising a glassy silica matrix having a BET surface area no greater than about 20 m$^2$/g and having macropores ranging in diameter from about 500 Å to about 4000 Å, the silica matrix comprising from about 25 to about 90 weight percent of the catalyst composition and having encapsulated therein domains of a catalytic component comprising magnesia and molybdenum oxide.

27. The process of preparing the catalyst of claim 26 comprising: (a) treating a source of magnesium oxide with a blocking agent, (b) adding the treated source of magnesium oxide to an alkali metal silicate solution, the silicate being present in a concentration sufficient to provide silica in an amount ranging from about 25 to about 90 weight percent of the catalyst composition, (c) polymerizing the silicate to form a composite comprising a glassy silica matrix having a BET surface area no greater than about 20 m$^2$/g and having macropores ranging from about 500 Å to about 4000 Å in diameter, the matrix containing domains of the treated source of magnesium oxide, (d) ion-exchanging the composite with an ammonium salt to reduce the concentration of alkali metal ions, (e) drying and calcining the composite under conditions sufficient to remove the blocking agent and sufficient to convert the source of magnesium oxide into magnesium oxide, (f) impregnating the domains of magnesium oxide with a source of an oxide of molybdenum, (g) calcining the resulting impregnated composite under conditions sufficient to convert the source of an oxide of molybdenum to an oxide of molybdenum.

28. The catalyst composition of claim 26 wherein the catalytic component contains a promoting amount of an alkali metal promoter.

29. The catalyst composition of claim 28 wherein the concentration of the alkali metal promoter ranges from about 0.01 weight percent to about 5 weight percent calculated as alkali metal hydroxide and based on the combined weights of silica, magnesium oxide and molybdenum oxide.

30. The catalyst composition of claim 28 wherein the alkali metal promoter is an alkali metal oxide, hydroxide, carbonate, acetate, or oxalate.

31. The catalyst composition of claim 28 wherein the alkali metal promoter is an oxide or hydroxide of potassium or cesium.

32. The catalyst composition of claim 26 wherein the crush strength is at least about 1.00 lb.

33. The process of preparing the catalyst of claim 28 comprising: (a) treating a source of magnesium oxide with a blocking agent, (b) adding the treated source of magnesium oxide to an alkali metal silicate solution, the silicate being present in a concentration sufficient to provide silica in an amount ranging from about 25 to about 90 weight percent of the catalyst composition, (c) polymerizing the silicate to form a composite comprising a glassy silica matrix having a BET surface area no greater than about 20 m$^2$/g and having macropores ranging from about 500 Å to about 4000 Å in diameter, the matrix containing domains of the treated source of magnesium oxide, (d) ion-exchanging the composite with an ammonium salt to reduce the concentration of alkali metal ions, (e) drying and calcining the composite under conditions sufficient to remove the blocking agent and sufficient to convert the source of magnesium oxide into magnesium oxide, (f) impregnating the domains of magnesium oxide with a source of an oxide of molybdenum and a source of an oxide of an alkali metal, (g) calcining the resulting impregnated composite under conditions sufficient to convert the sources of an oxide of molybdenum and oxide of alkali metal to an oxide of molybdenum and an oxide of alkali metal.

34. The process of claim 33 wherein the polymerization of the silicate is effected by the suspension polymerization method.

35. A process of preparing a composite material comprising a glassy silica matrix having a BET surface area no greater than about 20 m²/g and having macropores ranging from about 500 Å to about 4000 Å in diameter, the silica matrix having encapsulated therein domains of a metal oxide phase, the process comprising:

(a) treating a source of the metal oxide with a blocking agent, the metal oxide being selected from those reactive with an alkali metal silicate, (b) adding the treated source of the metal oxide to an alkali metal silicate solution, (c) polymerizing the silicate to form a composite comprising a glassy silica matrix having a BET surface area no greater than about 20 m²/g and having macropores ranging from about 500 Å to about 4000 Å in diameter, the matrix containing domains of the treated source of metal oxide phase, and (d) calcining the composite under conditions sufficient to remove the blocking agent and to convert the source of metal oxide into metal oxide.

36. The process of claim 35 wherein spheroidal particles are formed by the suspension polymerization method or by spray-drying.

37. The process of claim 35 wherein an ion-exchange procedure is conducted after the polymerization of the silicate (Step c) and before calcination (Step d) to reduce the concentration of alkali metal ions.

38. The process of claim 35 wherein the blocking agent is poly(vinyl alcohol), or a polyacrylic acid or polymethacrylic acid or salt thereof.

* * * * *

UNITED STATES PATENT AND TRADEMARK OFFICE
CERTIFICATE OF CORRECTION

PATENT NO. : 5,302,773
DATED : April 12, 1994
INVENTOR(S) : G. Edwin Vrieland, et al It is certified that error appears in the above-indentified patent and that said Letters Patent is hereby corrected as shown below:

In Claim 1, Col. 22, line 45, "0.60 lb, the catalyst composition comprising a glassy" should correctly read --0.60 lb, as measured on a particle having a size in the range from about 500 μm to about 800 μm, the catalyst composition comprising a glassy--.

In Claim 20, Col. 23, line 49, "crush strength of at least about 0.60 lb, said catalyst" should correctly read --crush strength of at least about 0.60 lb, as measured on a particle having a size in the range from about 500 μm to about 800 μm, said catalyst--.

UNITED STATES PATENT AND TRADEMARK OFFICE
CERTIFICATE OF CORRECTION

PATENT NO. : 5,302,773
DATED : April 12, 1994
INVENTOR(S) : G. Edwin Vrieland, et al It is certified that error appears in the above-indentified patent and that said Letters Patent is hereby corrected as shown below:

In Claim 25, Col. 24, line 5, "strength of the catalyst composition i3 at least about" should correctly read --strength of the catalyst composition is at least about--.

In Claim 26, Col. 24, line 9, "a crush strength of at least about 0.60 lb, the composition" should correctly read --a crush strength of at least about 0.60 lb, as measured on a particle having a size in the range from about 500 µm to about 800 µm, the composition--.

Signed and Sealed this

Sixth Day of June, 1995

BRUCE LEHMAN

*Attest:*

*Attesting Officer*    Commissioner of Patents and Trademarks